United States Patent [19]

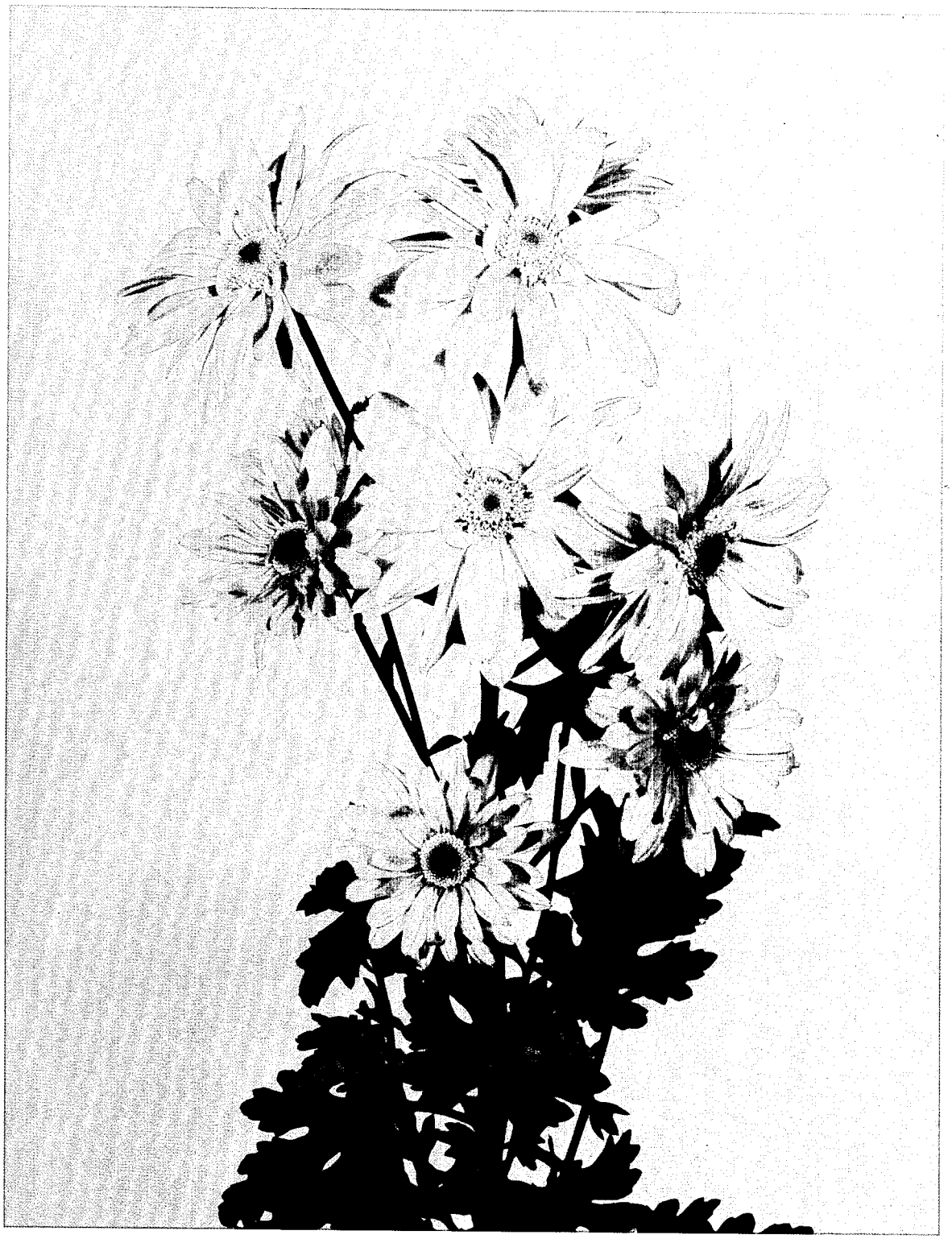

Meek et al.

[11] Plant 4,358

[45] Dec. 26, 1978

[54] CHRYSANTHEMUM PLANT

[75] Inventors: Jack M. Meek, Barberton; William E. Duffett, Akron, both of Ohio

[73] Assignee: Yoder Brothers, Inc., Barberton, Ohio

[21] Appl. No.: 781,413

[22] Filed: Mar. 25, 1977

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Donald D. Jeffery

[57] ABSTRACT

A mutation of the cultivar Camino Pink. All characteristics of Camino Coral are similar to the present cultivar except the ray floret color, which for Camino Coral is greyed-red, as contrasted with the lavender pink of Camino Pink.

1 Drawing Figure

The present invention comprises a new and distinct cultivar of *Chrysanthemum morifolium,* Ramat., hereinafter referred to by the cultivar name Camino Coral (#70309G24).

Camino Coral was discovered and selected by William E. Duffett and Jack M. Meek on May 10, 1974 as one plant (spontaneous mutant) within a flowering block of the parental cultivar, Camino Pink (#7309024; disclosed in our U.S. Plant patent application filed Nov. 5, 1976, Ser. No. 739,127) in a controlled environment in Barberton, Ohio.

The first act of asexual reproduction of Camino Coral was accomplished when vegetative cuttings were taken from the initial selection in November, 1974 in a controlled environment in Barberton, Ohio by a technician working under formulations established and supervised by Jack M. Meek and William E. Duffett. Horticultural examination of selected units initiated May 10, 1974 has demonstrated that the combination of characteristics as herein disclosed for Camino Coral are firmly fixed and are retained through successive generations of asexual reproduction.

Camino Coral has not been observed under all possible environmental conditions. The phenotype may vary significantly with variations in environment such as temperature, light intensity, and daylength. The following observations, measurements, and comparisons describe plants grown in Barberton, Ohio under greenhouse environmental conditions which approximate those generally used in commercial practice, as described in Chart A which appears at the end of the present specification. A light intensity chart of general use is shown in ASHAE Trans., Vol. 64, page 64, and reference is made thereto.

The following traits have been repeatedly observed and are determined to be basic characteristics of Camino Coral which in combination distinguish this chrysanthemum as a new and distinct cultivar:

1. Flat capitulum force.
2. Daisy capitulum type.
3. Greyed-red ray floret color.
4. Uniform nine week flowering response to photoperiodic short day control.
5. Medium plant height (requires 3–4 long day weeks as a single stem plant prior to short days to attain a total height as a flowering plant of 72 to 82 cm. during the flowering period October through May).

6. Diameter across face of capitulum from 60 to 80 mm. at maturity.
7. Semi-upright branching pattern.

The accompanying color photographic drawing shows typical inflorescence and foliage characteristics of Camino Coral. Color representations are as nearly true as possible with illustrations of this type. Some difficulty was encountered in obtaining the exact color representation in the color photograph of Camino Coral, the actual ray floret color being less pink and more grayed than that depicted in the color photograph. The color values set forth in the present specification are accurate.

Of the many commercial cultivars known to the present inventors, the most similar existing cultivars in comparison to Camino Coral is the parental cultivar, Camino Pink. Reference is made to attached Chart B which compares certain characteristics of Camino Pink with the same characteristics of Camino Coral. As noted in Chart B, the primary distinguishing characteristic of Camino Coral in comparison to Camino Pink is that of ray floret color. All other characteristics of Camino Coral are similar to those same characteristics of Panorama.

In the following description, color references are made to The Royal Horticultural Society Colour Chart. The color values were determined between 10:30 and 11:00 A.M. on Jan. 31, 1977 under 120 foot-candle light intensity at Barberton, Ohio.

Botanical classification: *Chrysanthemum morifolium,* Ramat., cv Camino Coral.

I. INFLORESCENCE

A. Capitulum:
- *Form.*—Flat.
- *Type.*—Daisy.
- *Diameter across face.*—60 to 80 mm.

B. Corolla of ray florets:
- *Color (abaxial).*—182B to 181D.
- *Color (adaxial).*—181D over 162C.

C. Corolla of disc florets:
- *Color (immature).*—137A to 144A.
- *Color (mature).*—144A to 7A.

D. Reproductive organs:
- *Androecium.*—Present disc florets only.
- *Gynoecium.*—Present both ray and disc florets.

II. PLANT

A. General appearance: Semi-upright branching pattern; medium height.

B. Foliage

*Color (abaxial).*—139A to 137A.

*Color (adaxial).*—137A to 137C.

CHART A

AVERAGE GREENHOUSE CHRYSANTHEMUM ENVIRONMENTS USED FOR BARBERTON, OHIO

| SEASON | TEMPERATURES USED Night | Bright Day | Cloudy Day | LIGHTING USED | BLACK CLOTH USED | SUPP $CO_2$ |
|---|---|---|---|---|---|---|
| FALL | 65° F to 56° F | 65° F to 80° F | 60° F to 75° F | 2 to 4 weeks at 3 Hours Per Night of 7–10 f.c. | To Sept. 15 on - 5:30 PM Off-7:30 AM | From Oct. 15 300 ppm |
| WINTER | 58° F to 62° F | 65° F to 70° F | 60° F to 65° F | 2 to 5 weeks at 5 hours Per Night of 7–10 f.c. | NONE | 300 ppm. |
| SPRING | 58° F to 65° F | 65° F to 80° F | 60° F to 75° F | 2 to 4 weeks at 5 Hours Per Night of 7–10 f.c. | From Mar. 15 on - 5:30 PM Off-7:30 AM | To Apr. 15 300 ppm |
| SUMMER | 62° F to 68° F | 70° F to 90° F | 65° F to 75° F | 1 to 2 weeks at 3 Hours Per Night of 7–10 f.c. | on-6:00 PM Off-8:00 AM | NONE |

CHART B

COMPARISON OF CAMINO CORAL AND CAMINO PINK

| CULTIVAR | RAY FLORET COLOR | DIAMETER ACROSS FACE OF CAPITULUM | PLANT HEIGHT | BRANCHING PATTERN | FLOWERING RESPONSE PERIOD | CAPITULUM FORM AND TYPE |
|---|---|---|---|---|---|---|
| CAMINO CORAL | Greyed-red | 60 to 80 mm. | Medium | Semi-upright | 9 week | Flat daisy |
| CAMINO PINK | Lavender pink | 60 to 80 mm. | Medium | Semi-upright | 9 week | Flat daisy |

COMPARISONS MADE OF PLANTS GROWN IN A GREENHOUSE IN BARBERTON, OHIO UNDER ENVIRONMENTAL CONDITIONS AS DESCRIBED IN CHART A.

We claim:

1. A new and distinct cultivar of *Chrysanthemum morifolium;* Ramat, known by the cultivar name Coralama and particularly characterized as to uniqueness by the combined characteristics of flat capitulum form, daisy capitulum type, greyed-red ray floret color, uniform nine week flowering response to photoperiodic shortday control, medium plant height, diameter across face of capitulum from 60 to 80 mm. at maturity, and semi-upright branching pattern.

* * * * *

UNITED STATES PATENT AND TRADEMARK OFFICE

CERTIFICATE OF CORRECTION

PATENT NO. : PP-4358

DATED : December 26, 1978

INVENTOR(S) : JACK M. MEEK and WILLIAM E. DUFFETT

It is certified that error appears in the above-identified patent and that said Letters Patent are hereby corrected as shown below:

In column 2, line 25, "Panorama" should be "Camino Pink".

In the claim, column 4, line 3, "Corolama" should be "Camino Coral".

Signed and Sealed this

*First* Day of *May 1979*

[SEAL]

*Attest:*

RUTH C. MASON
*Attesting Officer*

DONALD W. BANNER
*Commissioner of Patents and Trademarks*